United States Patent [19]
Melker et al.

[11] Patent Number: 5,601,559
[45] Date of Patent: *Feb. 11, 1997

[54] INTRAOSSEOUS NEEDLE

[75] Inventors: Richard J. Melker; Peter F. Gearen; Gary J. Miller, all of Gainesville, Fla.; Michael P. DeBruyne, Bloomington, Ind.; Lisa Molitor, Gainesville, Fla.

[73] Assignees: Cook Incorporated, Bloomington, Ind.; University of Florida Research Foundation, Gainesville, Fla.

[*] Notice: The term of this patent shall not extend beyond the expiration date of Pat. No. 5,431,655.

[21] Appl. No.: 192,006

[22] Filed: Feb. 4, 1994

Related U.S. Application Data

[63] Continuation-in-part of Ser. No. 74,216, Jun. 9, 1993, Pat. No. 5,431,655, which is a continuation of Ser. No. 884,323, May 11, 1992, Pat. No. 5,484,442, which is a continuation of Ser. No. 627,020, Dec. 13, 1990, abandoned, which is a continuation-in-part of Ser. No. 261,699, Oct. 24, 1988, abandoned.

[51] Int. Cl.$^6$ ........................................... A61B 5/00
[52] U.S. Cl. .......................... 606/79; 604/264; 606/191
[58] Field of Search .................................. 606/53, 86, 87, 606/88, 185, 72, 73, 74, 79, 80; 604/272–274, 164, 165, 51, 93

[56] References Cited

U.S. PATENT DOCUMENTS

| | | |
|---|---|---|
| 1,273,665 | 7/1918 | Porter . |
| 2,243,718 | 5/1941 | Moreira . |
| 2,525,329 | 10/1950 | Wyzenbeek . |
| 2,639,484 | 5/1953 | Wartman . |
| 2,667,682 | 2/1954 | Stone . |
| 3,090,384 | 5/1963 | Baldwin et al. . |
| 3,385,300 | 5/1968 | Holter . |
| 3,645,268 | 2/1972 | Capote . |
| 3,750,667 | 8/1973 | Pshenichny ............................ 604/164 |

(List continued on next page.)

FOREIGN PATENT DOCUMENTS

| | | |
|---|---|---|
| 2138152 | 5/1972 | France . |
| 2466994 | 4/1981 | France . |
| 265433 | 10/1913 | Germany . |
| 749088 | 1/1945 | Germany . |
| 1541237 | 7/1973 | Germany . |
| 2218901 | 8/1980 | Germany . |
| 48-40288 | 6/1973 | Japan . |
| 52-53198 | 1/1977 | Japan . |
| 1315796 | 5/1973 | United Kingdom . |
| 2130890 | 6/1984 | United Kingdom . |

OTHER PUBLICATIONS

Advertisement from Brookstone Catalog 1992, p. 55, self-drilling anchor.
Spivey, William H., "Intraosseous Infusions," The Journal of Pediatrics 111(5):639–643, Nov. 1987.
Tocantins, L. M. et al., "Infusions of Blood and Other Fluids Via the Bone Marrow," Journal of American Medical Association 117(15):1229–1234, Oct. 11, 1941.

*Primary Examiner*—Michael A. Brown
*Attorney, Agent, or Firm*—Woodard, Emhardt, Naughton, Moriarty & McNett

[57] ABSTRACT

An intraosseous needle having a threaded shaft with a passageway extending substantially therethrough, a solid and pointed tip at one end thereof, the tip having a plurality of cutting edges which facilitate boring through a bone. The shaft also includes two side ports in communication with the passageway to allow fluids to pass through the needle into the interior of the Done after successful insertion thereof. There is a hub at the opposite end of the shaft, whereby the needle is adapted to couple with an appropriate gripping device. A handle is provided in the shape of a ball knob and is adapted to telescopically and grippingly receive the hub of the needle. The hub and handle are both equipped with mutually engaging torque-transmitting surfaces. Additionally, the threads of the intraosseous needle may optionally be tapered so that at least one thread at the proximal end of the threaded shaft has a greater major (and/or minor) diameter than at least one thread located at the distal end of the threaded shaft. As the needle is inserted, the tapering of the threads provides a tighter fit between the bone and the needle to prevent needle wobble and fluid leakage.

34 Claims, 4 Drawing Sheets

U.S. PATENT DOCUMENTS

| | | |
|---|---|---|
| 3,815,605 | 6/1974 | Schmidt et al. . |
| 3,821,956 | 7/1974 | Gordhamer . |
| 3,859,998 | 1/1975 | Thomas et al. . |
| 4,191,191 | 3/1980 | Auburn . |
| 4,414,966 | 11/1983 | Stednitz ................................. 606/73 |
| 4,590,929 | 5/1986 | Klein . |
| 4,601,710 | 7/1986 | Moll . |
| 4,625,717 | 12/1986 | Covitz . |
| 4,654,030 | 3/1987 | Moll et al. . |
| 4,666,438 | 5/1987 | Raulerson . |
| 4,670,008 | 6/1987 | Von Albertini ........................ 604/165 |
| 4,722,261 | 9/1988 | Von Hoff et al. . |
| 4,790,817 | 12/1988 | Luther . |
| 4,803,982 | 2/1989 | Baker . |
| 4,826,492 | 5/1989 | Magasi . |
| 4,934,935 | 6/1990 | Edwards . |
| 4,944,677 | 7/1990 | Alexandre . |
| 4,969,870 | 11/1990 | Kramer et al. . |
| 5,082,445 | 1/1992 | Singer . |

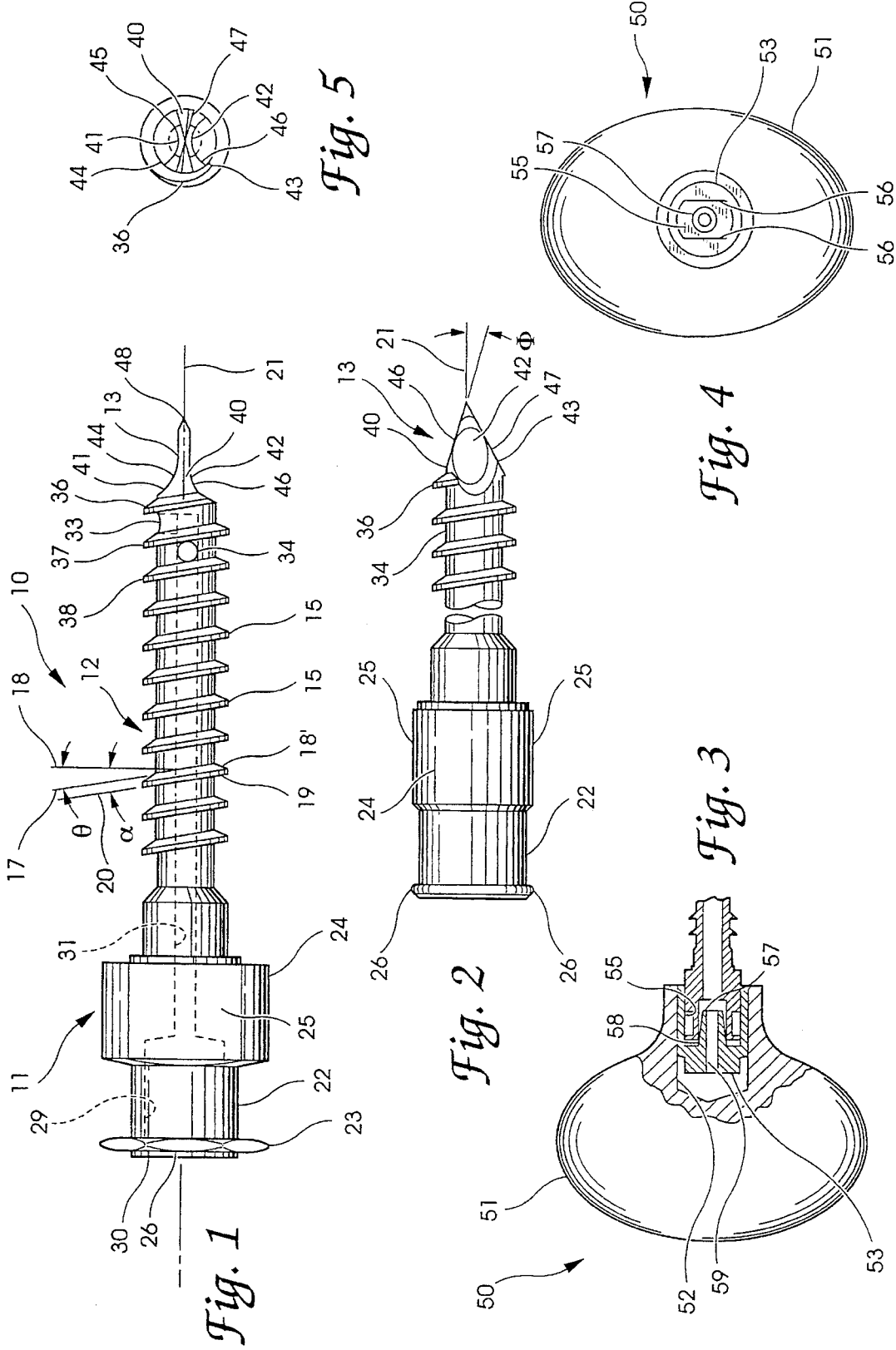

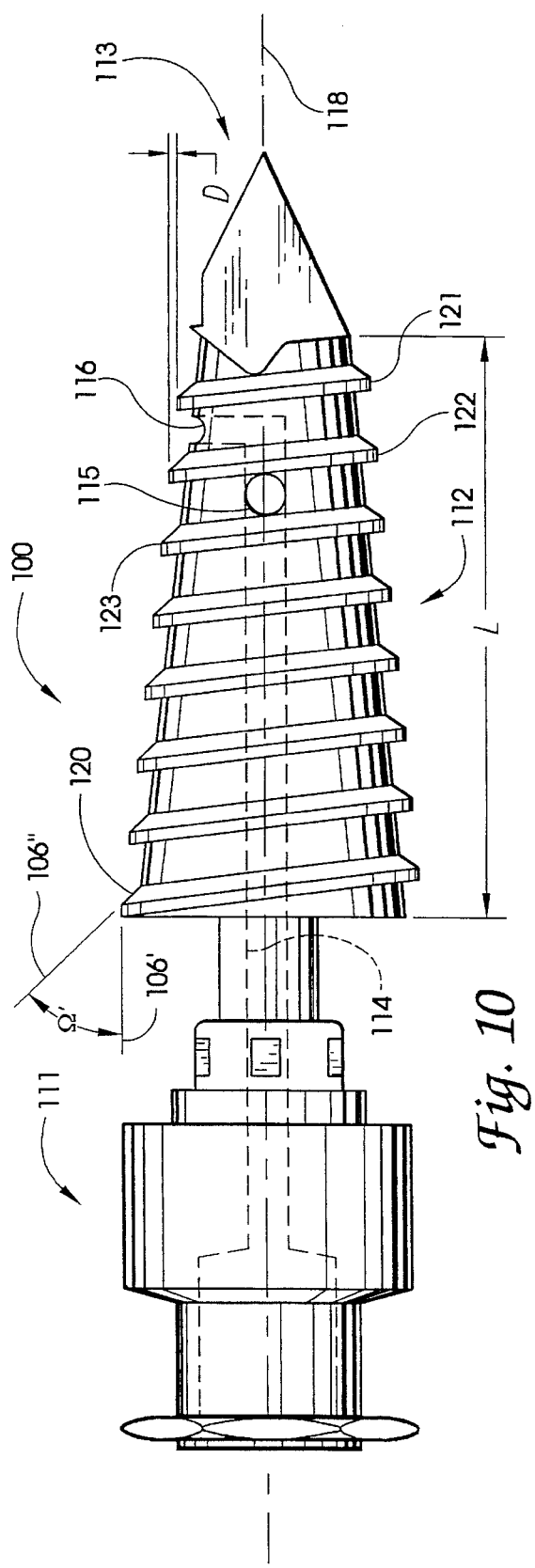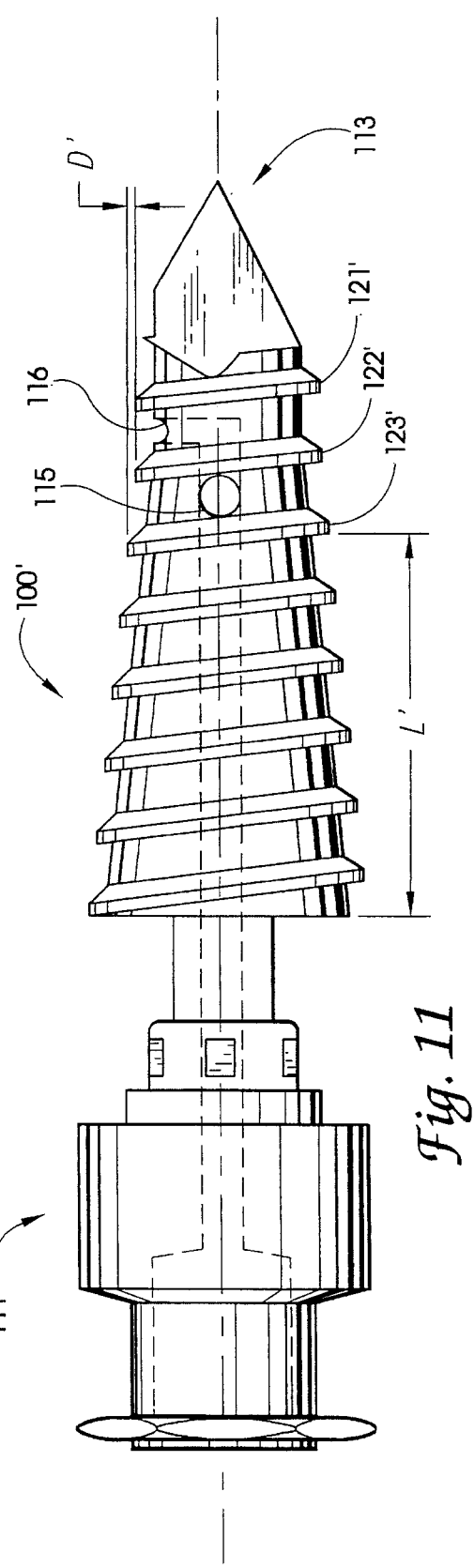

INTRAOSSEOUS NEEDLE

REFERENCE TO RELATED APPLICATIONS

This application is a continuation-in-part of of patent application Ser. No. 08/074,216 filed Jun. 9, 1993, now U.S. Pat. No. 5,431,655 which is a continuation of patent application Ser. No. 07/884,323 filed May 11, 1992, now U.S. Pat. No. 5,484,442, which is a continuation of U.S. patent application Ser. No. 07/627,020 filed Dec. 13, 1990, now abandoned, which is a continuation-in-part of patent application Ser. No. 261,699, filed on Oct. 24, 1988 (now abandoned) by the same inventive entity, and entitled Intraosseous Needle Assembly.

FIELD OF THE INVENTION

The present invention relates to infusion needles, and more particularly, to an intraosseous infusion needle having a tip adapted to bore directly into the patient's bone.

BACKGROUND OF THE INVENTION

In a variety of medical emergencies, the patient's life may hinge upon the ability of the physician or medical attendant to administer a particular fluid into the patient's bloodstream. In emergency situations such as on the battlefield, at traffic accident scenes or in the emergency room, the patient is often in shock, has low blood pressure, is bleeding profusely and may be thrashing about. Under such circumstances, finding and gaining access to a suitable blood vessel can be all but impossible, the resulting delay in administering drugs to the patient possibly being fatal. In the case of children or infants in any emergency, even the largest veins are so small that they may not be located. Even if located, an infant's largest available vein may be so small that stable infusion access may not be possible.

One alternative to venous access, recently reintroduced, is the intraosseous route. The medullary cavity of the long bones is composed of a rich spongy network of venous sinusoids which drain into a central venous canal. Blood then exits the venous canal by nutrient or emissary veins into the circulation. Fluids or drugs injected into the medullary area usually diffuse only a few centimeters, enter the bloodstream and reach the heart—all in only about 10 seconds from injection into the medullary cavity. It is important that any devices which provide intraosseous access have a lumen of a size adequate to allow for the infusion of relatively large volumes of fluid over a short period of time. Current intraosseous infusion procedures (meaning before the improvement described herein) utilize a hollow needle having a beveled tip and a trocar or stylet. With the stylet telescopically positioned within and extending partially out the bevelled end of the needle, the needle and trocar assembly is forceably and perpendicularly advanced against and through the desired bone until the cortex has been punctured and the needle and trocar tip has advanced into the medullary space. The trocar is then withdrawn, leaving the open end of the needle directly in the rich vascular network. Various complications, however, have made intraosseous infusion a less than ideal option. Although the needle and trocar assembly have a sharp, pointed tip, the medullary cavity may not be able to be penetrated under normal pressure. Too much force in trying to puncture the bone sometimes results in a bent needle, a broken needle, splintering of the bone, sliding off the bone and puncturing adjacent tissue or, more commonly, the needle is accidentally forced through the opposite side of the bone. Even if the needle is properly inserted into the medullary cavity, movements by the patient can easily dislodge the needle or cause it to be moved so that the end opening is occluded. These complications commonly arise in cases involving intraosseous infusion of infants and children. Additionally, fluid may leak from the puncture site into surrounding tissues. For persons older than six, the bones are too hard to successfully perform intraosseous infusion utilizing current procedures without realizing an extremely high incidence of the above complications. The current procedure has, therefore, typically been limited to children less than six years old and only after several attempts have been made to achieve venous infusion.

What is needed is an intraosseous infusion device which decreases the incidence and severity of the above described complications, which is easier to insert, which is more stable once inserted, prevents leakage of infused fluids, and, most importantly, which can be used in subjects of all ages.

SUMMARY OF THE INVENTION

Generally speaking, there is provided an intraosseous needle which allows for precise control and placement of the needle during intraosseous infusion procedures.

An intraosseous needle has a threaded shaft with a passageway extending substantially therethrough. At the leading end of the shaft is a solid pointed tip having a plurality of cutting edges, one of which coincides at a point with a thread to allow the threads to catch once the boring is completed. In the preferred embodiment, the tip is shaped like a three sided pyramid and is adapted for rapid and precise boring into the bone of adults, children or infants. The shaft further defines a pair of side ports, one located in the valley between the leading or first full thread and the second thread and the other side port located between the second thread and the third thread. The side ports are located 270° apart and are both in communication with the passageway of the shaft. A handle in the shape of a ball knob is adapted for telescopic and gripping connection to the trailing end of the needle and both the handle and the trailing end of the needle are equipped with mutually engaging, torque-transmitting faces.

Additionally, a tapered intraosseous needle is provided wherein the outer diameter of the most proximal thread located on the shaft is greater than the outer diameter of the most distal thread on the shaft. Tapering the threads as described allows for greater needle stability and prevents leakage from the insertion point, which may be due to the creation of a larger hole than is necessary during needle insertion.

It is an object of the present invention to provide an improved intraosseous needle which reduces the incidence and severity of the complications attendant in current procedures and devices.

It is another object of the present invention to provide an intraosseous needle which is easy to use.

It is still another object of the present invention to provide an intraosseous needle which is more stable once inserted.

It is still another object of the present invention to provide an intraosseous needle which is suitable for use in subjects of all ages.

Further objects and advantages of the present invention will become obvious from the following description of the preferred embodiments.

BRIEF DESCRIPTION OF THE DRAWINGS

FIG. 1 is a plan view of an intraosseous needle in accordance with one embodiment of the present invention.

FIG. 2 is a fragmented plan view of the needle of FIG. 1 which has been rotated 90° about its axis.

FIG. 3 is a plan view, partly in section, of a handle and intraosseous needle of the present invention.

FIG. 4 is a front view of the handle of FIG. 3.

FIG. 5 is a front end view of the intraosseous needle of FIG. 1.

FIG. 10 is a plan view of an intraosseous needle in accordance with another embodiment of the present invention.

FIG. 11 is a plan view of an intraosseous needle in accordance with a further embodiment of the present invention.

DESCRIPTION OF THE PREFERRED EMBODIMENTS

Figure 7:
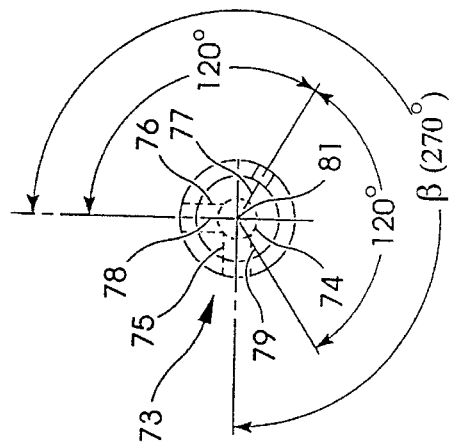
FIG. 7 is a front end view of the intraosseous needle of FIG. 6 showing the angular relationships between side ports and cutting edges.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIGS. 1 and 2 there is shown an intraosseous needle 10 in accordance with one embodiment of the present invention. Needle 10 includes a hub 11, a threaded shaft 12 and boring means. In this embodiment, the boring means is a fluted pencil point hip 13. Behind the boring means, there are 0.150–16 buttress threads 15 on shaft 12 having a major diameter of 0.150" and a minor diameter of 0.110", both to a tolerance of 0.005". Recall that the threads are shaped to ensure that the needle is stable and prevents leakage once inserted. The lead angle or helix angle $\theta$ is defined as the angle formed by a plane (indicated at 17) drawn tangent to the pitch helix and a plane (indicated at 18) normal to the axis 21 of threaded shaft 12. The leading and trailing thread surfaces are indicated at 18' and 19, respectively. The trailing thread angle $\alpha$ is defined here as that angle formed by a plane (indicated as 20) drawn tangent to trailing thread surface 19 and plane 18 normal to axis 21. Trailing thread angle $\alpha$ in the preferred embodiment is equal to the helix angle $\theta$. That is, plane 17 is parallel to plane 20. As shown in the embodiment of FIG. 1, trailing thread angle alpha is approximately 8°, while leading surface 18' forms an angle with normal plane 18 of about 30°, that is, leading and trailing surfaces 18' and 19 are not parallel.

Hub 11, located at the rearward or trailing end of threaded shaft 12, forms the female end for connection to a conventional Luer-type fitting and includes a generally cylindrical portion 22 and an annular flange portion 23. A generally cylindrical section 24 is located between cylindrical portion 22 and threaded shaft 12. The diameters of flange portion 23 and cylindrical section 24 are approximately equal and both are greater than the diameter of cylindrical portion 22. Cylindrical section 24 has a pair of diametrically opposed and mutually parallel flat faces 25. Flange portion 23 likewise has a pair of diametrically opposed and mutually parallel flat faces 26 which are coplanar with corresponding flat faces 25. A large diameter bore 29 with a standard Luer taper is defined in hub 11 and extends from end 30 through cylindrical portion 22 and partially through cylindrical section 24. Bore 29 receives the male portion of the Luer-type fitting. A smaller diameter axial passageway 31 is in communication with bore 29 and extends from bore 29 forwardly through nearly the entire length of threaded shaft 12. A pair of side ports 33 and 34 extend radially outwardly from axial passageway 31 near tip 13. Side ports 33 and 34 are located 90° apart. Side port 33 opens outwardly in the valley between the leading or first full thread 36 and the second thread 37. Side port 34 opens outwardly in the valley between the second thread 37 and the third thread 38.

Fluted pencil point tip 13 is substantially conical with the conical outer surface 40 forming an angle $\Phi$ with axis 21 of approximately 20°. A pair of diametrically opposed flutes 41 and 42 are milled into the end of tip 13 using a ball end mill. The end mill used to cut flutes 41 and 42 is aligned to rotate about an axis which is parallel with axis 21 during the milling process. The foremost end 43 of leading thread 36 is interrupted by the milling process such that leading thread 36 terminates into one of the flutes 42. The milling process thus forms sharp boring edges 44 and 45 between flute 41 and conical surface 40 and sharp boring edges 46 and 47 between flute 42 and conical surface 40. The border between leading thread 36 and flute 42 likewise forms a sharp cutting edge at 43. As shown in FIG. 1, flute 42 is machined further rearwardly than flute 41. In the present embodiment, the complete axial length of flute 41 measured from tip 48 is 0.14 inches while the complete axial length of flute 42 measured from tip 48 is 0.16 inches.

A complete intraosseous needle assembly includes, along with intraosseous needle 10, a corresponding gripping means or gripping element which is handle 50 (FIGS. 3 and 4). Handle 50 comprises a plastic ball knob 51 having an axial bore 52. An insert 53 for gripping needle 10 is sized to be tightly received within bore 52. Insert 53 is fixed within bore 52 by appropriate means such as by gluing. Insert 53 is adapted to couple with needle 10 and has a central opening 55 which is generally cylindrical with opposing planar faces 56. Opening 55 is sized to receive the complimentary shape of hub 11 with its cylindrical section 24 and opposing flat faces 25. Insert 53 further includes stub 57 which extends forwardly into opening 55. As hub 11 of needle 10 is received within opening 55, stub 57 enters bore 29 of hub 11. Stub 57 is stepped slightly forwardly such that its largest diameter, at its base 58, is the same as or just slightly larger than the inner diameter of bore 29. As stub 57 advances into hole 29, the larger diameter at base 58 of stub 57 wedges within bore 29 forming a snug fit between needle 10 and handle 50. Hub 11, bore 29, opening 55 and stub 57 are sized to create a mutually snug connection sufficient to cause hub 11 to remain firmly lodged within handle 50 but to be removed under a moderate manually applied tensile force.

Figure 6:
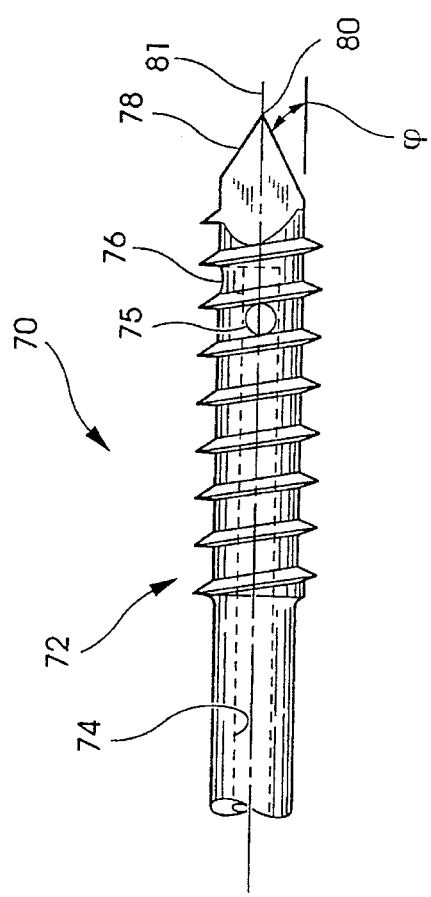
FIG. 6 is a fragmented plan view of an intraosseous needle in accordance with the preferred embodiment of the present invention.
Figure 8:
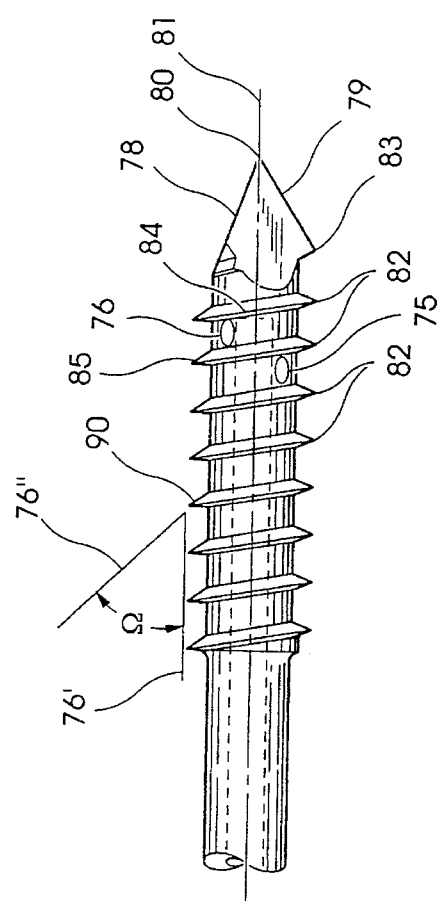
FIG. 8 is a plan view of the intraosseous needle of FIG. 6 rotated about its axis to show the cutting edge which coincides at a point with the ridgeline defined by the threads.
Figure 9:
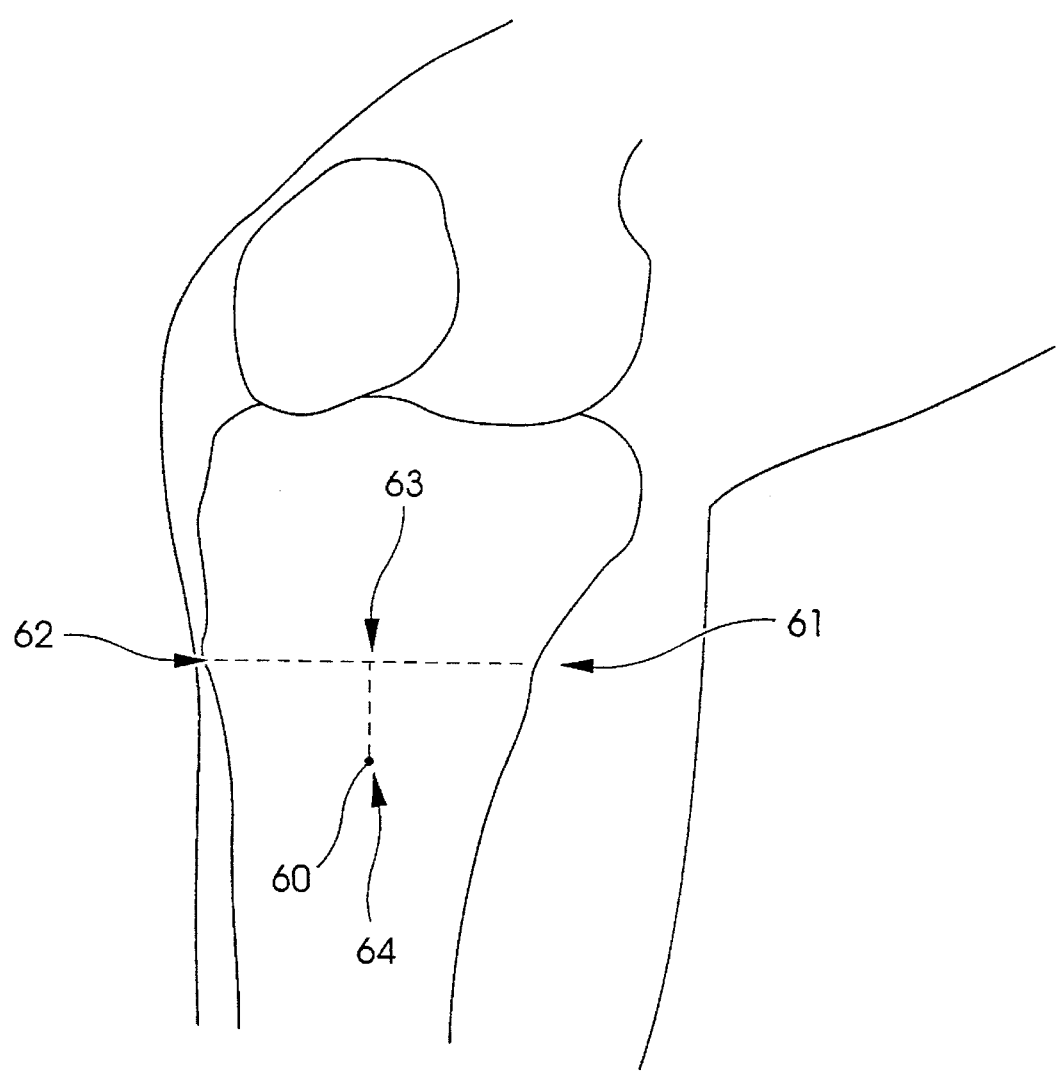
FIG. 9 is a diagrammatic side view of the proximal tibia showing the preferred access site of the present invention.

Referring now to FIGS. 6, 7 and 8, there is shown an intraosseous needle 70 in accordance with a preferred embodiment of the present invention. Needle 70 includes a hub, not shown but identical to hub 11 described earlier, a threaded shaft 72 and a boring end 73. Like the embodiment described earlier, shaft 72 includes an axial passageway 74 in communication with side ports 75 and 76. Also, the thread size is identical to the embodiment described earlier, which ensures the stability of the needle once implanted and the patency of the side ports (described infra). Like the embodiment described above, the thread angle Ω is approximately 45°. The thread angle Ω is the angle measured between a line 76' parallel to axis 81 and a line 76" which extends through the axis 81 and is coextensive with the face 90 of the thread. The boring end 73 is formed in the shape of a regular three-sided pyramid wherein the three cutting edges 77, 78 and 79 culminate in pointed tip 80. Cutting edges 77, 78 and 79 are 120° apart about axis 81, which is defined by the needle. Boring end 73 can be formed by grinding or any other suitable means which leaves cutting edges 77, 78 and 79 relatively sharp. The grind angle c, which in this case is approximately 24°, defines the slope of each side of the pyramid. The boring end 73 is precision ground so that cutting edge 79 coincides with helical thread ridgeline 82 at point 83. This arrangement couples boring end 73 to threaded shaft 72, allowing the threads to engage the bone when the boring is completed.

Also of significance is the location of side ports 75 and 76 with respect to both the threads of shaft 72 and the cutting edges of boring end 73. Side ports 75 and 76 must be sized and situated to avoid the risk that they might become clogged with tissue during insertion of needle 70 into bone in order to ensure that potentially life-saving fluids can be passed thru the needle to the desired location within the bone. With this in mind, side port 76 is axially aligned with cutting edge 78 and is located in the valley between the first two successive threads 84 and 85 which are uninterrupted by the surfaces and edges forming boring end 73. Side port 75 is likewise situated between two adjacent threads but is angularly displaced about axis 81 from side port 76. This angle B is approximately 270°.

Referring now to FIGS. 10 and 11, there are shown two further embodiments of the intraosseous needle of the present invention. More specifically, FIG. 10 shows one embodiment of the intraosseous needle of the present invention, wherein the the major diameter of the helical ridgeline of the threads is continuously increased so as to cause the threads on the intraosseous needle to be tapered. Additionally, the minor diameter of the thread may be tapered, as is described in connection with the major diameter of the thread.

As with needle 70, intraosseous needle 100 includes a hub 111, virtually identical to hub 11 described in connection with FIGS. 1–3, a threaded shaft 112 and a boring end 113. Additionally, as with the earlier described embodiments, shaft 112 includes an axial passageway 114 in communication with side ports 115 and 116. The intraosseous needle 100 is shown incorporating the same type of boring end 113 as is described in connection with FIGS. 6–8, including a helical thread ridgeline and a point located where the helical thread ridgeline coincides with the desired cutting edge. However, this is not meant to limit the present embodiment to the use of the above-described type of boring end. The boring end 113 may be formed either in the shape of a regular three-sided pyramid as presently shown, or may be formed in the shape of a fluted pencil point tip, as described in connection with FIGS. 1–5, but wherein the height of the helical thread ridgeline is continuously increasing. Additionally, other types of boring ends may be used. Further, the operation of the boring end 113 would be much the same as that of the boring end of needles 10 and 70, depending upon which boring end type was chosen.

Unlike the intraosseous needle embodiments shown in FIGS. 1–8, the present embodiment includes a threaded shaft 112 wherein, due to the continuously increasing height of the helical thread ridgeline, the major diameter of each successive thread (and optionally, the minor diameter) is greater than the major (and/or minor) diameter of the thread preceding it, starting from the thread nearest the boring end 113 and proceeding back towards the hub section 111 a length L along the shaft. For example, in FIG. 10, the height of the second full thread 122 is shown as being a height D greater than the height of the first full thread 121, resulting from the continuously increasing height of the helical thread ridgeline. Likewise, the height of the third full thread 123 would be increased by a height D from its immediately preceding thread 122.

As the height of the helical thread ridgeline of the intraosseous needle 100 is continuously increasing, the threads of the threaded shaft 112 include a taper on the thread diameter(s) of the needle 100 starting from the boring end 113 of the threaded shaft back towards the hub 111. In a preferred embodiment of the intraosseous needle of FIG. 10, the taper of the threads on the diameter over the length L, may increase from 0.0001 inch–0.1000 inch per inch of shaft length, and is preferably increased from between 0.010 inch—0.030 inch per inch, but is most preferably increased by 0.020 inch per inch of shaft.

Further, the taper on the thread in the present embodiment is accomplished by grinding the threads to have the desired major (and/or minor) diameters. Prior to grinding, the major and minor diameters of each specified thread are the same throughout the needle. As with the previously described embodiments, each thread may originally have a major diameter of 0.150" and a minor diameter of 0.110", both to a tolerance of 0.005", prior to grinding. Similarly, the threads may initially be 0.150–16 buttress threads. Note that for the purpose of this disclosure, if the phrase "the outer diameter of the leading thread" is used herein, it is meant to describe the outer diameter of the leading thread prior to milling.

As previously described in connection with FIGS. 1–8, the thread angle Ω, is approximately 45°. The thread angle Ω' is the angle measured between a line 106' parallel to axis 118 and a line 106" which extends through the axis 118 and is coextensive with the face 120 of the thread.

Additionally, as with the previous embodiments, the intraosseous needle 100 includes side ports 115 and 116, which are sized and situated to avoid the risk that they might become clogged with tissue during insertion of needle 100 into bone in order to ensure that potentially life-saving fluids can be passed thru the needle to the desired location within the bone. Again, side port 116 may be axially aligned with a cutting edge and is located in the valley between the first two successive threads 121 and 122 which are uninterrupted by the surfaces and edges forming boring end 113. Side port 115 is likewise situated between two adjacent threads but is angularly displaced about axis 118 from side port 116. This angle β (shown in FIG. 7) is approximately 270°.

In FIG. 11, there is shown a modified version of the tapered intraosseous needle 100', which is virtually identical to that of FIG. 10, with the exception that the taper on the threads may begin anywhere after the second sideport 115. Preferably, the taper will begin with the first thread 123' after the second sideport 115. As such the threads may be tapered for a distance L' over the shaft. Thus, at least the first full thread 121' and the second full thread 122' will have the same constant major diameter. As with the embodiment of FIG. 10, each thread may originally have had a major diameter of 0.150" and a minor diameter of 0.110", both to a tolerance of 0.005", prior to grinding to achieve the taper.

Further, The third full thread 123' would have a height D' greater than the previous two full threads, 121' and 122'. As with the embodiment of FIG. 10, the continuously increasing taper on the diameter of the thread of the intraosseous needle 100', may be within the range of 0.0001 inch–0.1000 inch per inch of shaft length, and is preferably between 0.010 inch–0.030 inch per inch, but is most preferably 0.020 inch per inch.

Additionally, as with the embodiment shown in FIG. 10, the boring end 113 may be formed either in the shape of a regular three-sided pyramid as presently shown, which configuration is described herein in connection with FIGS. 6–8, or may be formed in the shape of a fluted pencil point tip, as described in connection with FIGS. 1–5. All other features are identical to that described in connection with the above described embodiments.

In operation, the increasing taper on the threads shown and described in connection with the embodiments of FIGS. 10 and 11, causes a small hole (relative to the later thread diameter) to initially be drilled into the bone. Thus, the fit between the needle and the bone is made tighter as the needle is screwed in to the insertion site. This tight fit helps to seal the insertion site thus preventing extravasation and aids in stabilizing the needle in the bone.

The intraosseous needle assembly is used as follows:

An intraosseous needle 10, 70, 100 or 100' is firmly secured to a handle 50. The preferred site is marked and an incision is made in the skin down to the bone. The preferred site 64 is found by first identifying the tibial tuberosity 62 on the anterior surface of the proximal tibia. An imaginery line is drawn from the tibial tuberosity to the median edge of the tibia 61. This line is equally divided 63 and the site of insertion 64 is perpendicular and distal to 63. The preferred site 64 increases in distance from 63 with increasing age. In the newborn or infant this distance may be as short as 0.3–0.5 cm and increases to approximately 2.5 cm by 6 years of age. Insertion at the level of the tibial tuberosity or distally, avoids insertion of the needle into the growth plate of the tibia. The distal medial tibia is also an excellent site.

With handle 50 firmly in the palm of the operator's hand, the needle is selectively directed toward the desired access site 63 and contact with the bone is made. A back and forth twisting motion with slight pressure causes the four cutting edges 44–47, or the three cutting edges 77–79, to cut into the bone. In other words, cutting edges 45 and 46 engage and cut into the bone when the needle is rotated clockwise, and cutting edges 44 and 47 engage and cut into the bone when the needle is rotated counterclockwise. This enables flutes 41 and 42, as well as cutting edges 77–79, to penetrate to the threaded section of the needle. During the twisting motion, flutes 41 and 42, as well as the pyramid surfaces in the preferred embodiment, carry bone fragments out of the hole. Once the lead thread 36 of needle 10 reaches the hole 60, no further pressure is required. In the case of needle 70, the back and forth twisting motion is continued until point 83 engages the bone. In other words, cutting edges 77, 78 and 79 cut into the bone when the needle is twisted clockwise and counterclockwise until point 83 of helical ridgeline 82 engages the bone. After engaging the threads, the operator simply screws the needle clockwise into the marrow to the desired depth. Obviously the size of the patient will determine how far to screw the needle in. As the needle is rotatably advanced, the design of the threads directs the marrow out and away from the side ports. A fluid injected through needle 10, 70, 100 or 100', may then exit through side ports 33 and 34, or 75 and 76, unobstructed by marrow or other tissue which otherwise clogs conventional intraosseous needles.

With needle 10, 70, 100 or 100' in the desired position, handle 50 may be detached from the needle by slight, manually applied, tensile pressure therebetween. The appropriate drug administering mechanism such as a syringe or I.V. tubing may then be secured via the Luer-type fitting. After the patient has stabilized, venous access may be achieved and needle 10, 70, 100 or 100' may be removed by detaching the I.V. tubing or syringe from the needle and by re-securing handle 50 thereto. The needle 10, 70, 100 or 100' may then be backed out by turning the needle counterclockwise.

While the invention has been illustrated and described in detail in the drawings and foregoing description, the same is to be considered as illustrative and not restrictive in character. For example, in the embodiment of FIG. 11, it is shown that the thread taper on the needle begins after the second sideport and with the third full thread. However, it is contemplated that the taper on the major diameter (and, optionally, the minor diameter) of the threads could begin anywhere along the needle after the second sideport. It being understood that only the preferred embodiment has been shown and described and that all changes and modifications that come within the spirit of the invention are desired to be protected.

What is claimed is:

1. An intraosseous needle, comprising:

a threaded shaft having first and second opposing ends and a passageway extending from the first end toward the second end, said threaded shaft including a plurality of thread portions;

boring means for initiating penetration of said shaft into bone, said boring means formed as part of said second end;

wherein said shaft has at least one opening proximal to the second end and in communication with the passageway;

wherein said boring means is generally conical with a pointed tip;

wherein said boring means is solid and has at least two cutting edges;

wherein said at least one opening is a side port located behind said boring means;

wherein said boring means has a pair of concave indentations which define said at least two cutting edges; and wherein at least one thread portion proximal said first end has a greater major diameter than at least one thread portion proximal said second end.

2. The intraosseous needle of claim 1 wherein the thread portion nearest to said boring means being a leading thread portion and wherein at least one of said indentations interrupts the leading thread portion.

3. The intraosseous needle of claim 2 wherein the thread portion nearest to said leading thread portion has a greater major diameter than said leading thread portion.

4. The intraosseous needle of claim 2 wherein at least one thread portion adjacent said leading thread portion has the same major diameter of said leading thread portion.

5. The intraosseous needle of claim 3 wherein there are two side ports, each of which is located between two adjacent threads.

6. The intraosseous needle of claim 5 wherein said indentations define four cutting edges which enable said needle to cut into bone by rotating said needle in any direction about said axis.

7. The intraosseous needle of claim 6 wherein each of said threads has a helix angle and a trailing angle, the trailing thread angle and helix angle being substantially equal.

8. The intraosseous needle of claim 6 wherein said pair of concave indentations create four cutting edges, two of said four cutting edges for cutting upon rotation of said shaft in one direction about the axis and the other two of said four cutting edges for cutting upon rotation of said shaft in a direction opposite to the one direction.

9. An intraosseous needle, comprising:
 a threaded shaft having first and second opposing ends and a passageway extending from the first end toward the second end, said threaded shaft including a plurality of thread portions;
 boring means for initiating penetration of said shaft into bone, said boring means formed as a part of said second end;
 wherein said shaft has at least one opening proximal to the second end and in communication with the passageway;
 wherein said boring means is generally conical with a pointed tip;
 wherein said boring means is solid and has at least two cutting edges;
 wherein said at least one opening side port located behind said boring means;
 wherein said boring means has a pair of concave indentations which define said at least two cutting edges;
 wherein at least one thread portion proximal said first end has a greater major diameter than at least one thread portion proximal said second end;
 wherein the thread portion nearest to said boring means being a leading thread portion and wherein at least one of said indentations interrupts the leading thread portion; and
 wherein at least one thread of said shaft initially has a major diameter of 0.150 inches and a minor diameter of 0.110 inches and wherein the major diameter of each thread decreases from said first end of said threaded shaft towards said second end by 0.020 inch per inch of shaft length.

10. An intraosseous needle, comprising:
 a shaft having a plurality of threads, first and second opposing ends and a passageway extending from said first end toward said second end, said second end having a pointed tip and a plurality of cutting edges for initiating penetration of said shaft into bone; and
 wherein said shaft has at least one opening proximal to said second end and in communication with said passageway;
 wherein said threads define a helical ridgeline which coincides at a point with one of said cutting edges, said one of said cutting edges terminating at said point; and
 wherein at least one thread proximal said first end has a greater major diameter than at least one thread proximal said second end.

11. The intraosseous needle of claim 10 wherein said second end is formed in the shape of a three sided pyramid having three edges which intersect at said pointed tip, wherein said three edges are three said cutting edges.

12. The intraosseous needle of claim 10 wherein said shaft has first and second threads that are uninterrupted by said cutting edges, said at least one opening is a first side port located between said first and second threads.

13. The intraosseous needle of claim 12 wherein said first thread has a greater major diameter than said second thread.

14. The intraosseous needle of claim 12 wherein the major diameter of said first thread is equal to the major diameter of said second thread.

15. The intraosseous needle of claim 10 wherein said at least one opening includes a second side port located between two adjacent threads and behind said second thread.

16. The intraosseous needle of claim 12 wherein said shaft defines an axis, and said second side port is further located at an angle of approximately 270° about said axis from said first side port.

17. The intraosseous needle of claim 12 wherein said first side port is axially aligned with one of said cutting edges.

18. The intraosseous needle of claim 17 wherein said at least one opening includes a second side port located between two adjacent threads and behind said second thread.

19. The intraosseous needle of claim 18 wherein said shaft defines an axis, and said second side port is further located at an angle of approximately 270° about said axis from said first side port.

20. The intraosseous needle of claim 17 wherein each of said threads has a thread angle of approximately 45°.

21. An intraosseous needle, comprising:
 a shaft having a plurality of threads, first and second opposing ends and a passageway extending from said first end toward said second end, said second end having a pointed tip and a plurality of cutting edges for initiating penetration of said shaft into bone; and
 wherein said shaft has at least one opening proximal to said second end and in communication with said passageway;
 wherein said threads define a helical ridgeline which coincides at a point with one of said cutting edges, said one of said cutting edges terminating at said point;
 wherein at least one thread proximal said first end has a greater major diameter than at least one thread proximal said second end;
 wherein said shaft has first and second threads that are uninterrupted by said cutting edges, said at least one opening is a first side port located between said first and second threads;
 wherein said first side port is axially aligned with one of said cutting edges;
 wherein each of said threads has a thread angle of approximately 45°; and
 wherein at least one thread originally has a major diameter of 0.150 inches and a minor diameter of 0.110 inches, and wherein the major diameter of said threads decreases from said first end towards said second end by 0.020 inch per inch of shaft length.

22. An intraosseous needle, comprising:
 a shaft having a plurality of threads, first and second opposing ends and a passageway extending from said first end toward said second end, wherein said threads have a thread angle of approximately 45° and define a helical ridgeline, and said second end formed in the shape of a three-sided pyramid having a pointed tip and three edges for initiating penetration of said shaft into bone;
 wherein said helical ridgeline coincides at a point with a first one of said three edges to initiate engagement of said threads with the bone, said first one of said three edges terminating at said point;

wherein said shaft has a first side port and a second side port proximal to said second end and in communication with said passageway, said first side port axially aligned with a second one of said three edges of said three-sided pyramid and located between the first two adjacent said threads that are uninterrupted by said second one of said three edges, said second side port located between two adjacent said threads and situated at an angle of approximately 270° from said first side port about an axis defined by said shaft; and wherein a first thread proximal to said first end has a greater major diameter than a second thread proximal to said second end.

23. An intraosseous needle, comprising:

a threaded shaft having first and second opposing ends and a passageway extending from the first end toward the second end, said threaded shaft including a plurality of thread portions;

boring means for initiating penetration of said shaft into bone, said boring means formed as part of said second end;

wherein said shaft has at least one opening proximal to the second end and in communication with the passageway;

wherein said boring means is solid and has at least two cutting edges; and wherein at least one thread portion proximal said first end has a greater major diameter than at least one thread portion proximal said second end.

24. The intraosseous needle of claim 23 wherein said at least one thread portion proximal said first end has a greater major diameter than at least first and second thread portions proximal said second end, wherein said at least first and second thread portions proximal said second end are of equal major diameter.

25. The intraosseous needle of claim 24 wherein said first and second thread portions are adjacent.

26. The intraosseous needle of claim 25 wherein said boring means has a pair of concave indentations which define said at least two cutting edges, wherein said second thread portion is adjacent a leading thread portion, and wherein at least one of said indentations interrupts the leading thread portion.

27. The intraosseous needle of claim 26 wherein said first thread portion is distal from said leading thread portion.

28. The intraosseous needle of claim 26 wherein there are two side ports, each of which is located between two adjacent threads.

29. The intraosseous needle of claim 25 wherein said first thread portion is said leading thread portion, and wherein said major diameter of said second thread portion is equal to the major diameter of said leading thread portion prior to forming said indentations.

30. The intraosseous needle of claim 23 wherein said at least one thread portion proximal said first end has a greater major diameter than at least first and second thread portions proximal said second end, wherein said first thread portion is adjacent to said second thread portion, and wherein said first thread portion has a greater major diameter than said second thread portion.

31. The intraosseous needle of claim 30 wherein said second thread portion is the first full thread of said threaded shaft located nearest to said boring means.

32. The intraosseous needle of claim 31 wherein said boring means has a pair of concave indentations which define said at least two cutting edges, wherein said second thread portion is adjacent a leading thread portion, wherein at least one of said indentations interrupts said leading thread portion, and wherein the major diameter of said leading thread portion prior to forming said indentations is less than the major diameter of said second thread portion.

33. The intraosseous needle of claim 31 wherein said first thread portion is adjacent to said second thread portion.

34. The intraosseous needle of claim 33 wherein there are two side ports, each of which is located between two adjacent threads.

* * * * *